(12) United States Patent
Wimberger-Friedl et al.

(10) Patent No.: US 11,513,038 B2
(45) Date of Patent: Nov. 29, 2022

(54) SAMPLE HOLDER FOR BIOLOGICAL SAMPLES

(71) Applicant: KONINKLIJKE PHILIPS N.V., Eindhoven (NL)

(72) Inventors: Reinhold Wimberger-Friedl, Eindhoven (NL); Jacobus Hermanus Maria Neijzen, Eindhoven (NL); Anja Van De Stolpe, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 426 days.

(21) Appl. No.: 15/322,495

(22) PCT Filed: Jun. 29, 2015

(86) PCT No.: PCT/EP2015/064677
§ 371 (c)(1),
(2) Date: Dec. 28, 2016

(87) PCT Pub. No.: WO2016/001126
PCT Pub. Date: Jan. 7, 2016

(65) Prior Publication Data
US 2017/0138822 A1 May 18, 2017

(30) Foreign Application Priority Data
Jun. 30, 2014 (EP) .................................... 14175012

(51) Int. Cl.
*G01N 1/08* (2006.01)
*B01L 3/00* (2006.01)
(Continued)

(52) U.S. Cl.
CPC ............... *G01N 1/08* (2013.01); *B01L 3/502* (2013.01); *B01L 3/5027* (2013.01); *G01N 1/31* (2013.01);
(Continued)

(58) Field of Classification Search
CPC ... G01N 1/28; G01N 1/31; G01N 1/08; B01L 2200/026; A61B 2010/045; A61B 5/6848
See application file for complete search history.

(56) References Cited

U.S. PATENT DOCUMENTS

| | | | |
|---|---|---|---|
| 3,498,909 A | | 3/1970 | Littman |
| 3,634,651 A | * | 1/1972 | Siegel .................... B01L 7/00 219/386 |

(Continued)

FOREIGN PATENT DOCUMENTS

| | | |
|---|---|---|
| GB | 2289222 A | 11/1995 |
| JP | 2002303568 A | 10/2002 |

(Continued)

OTHER PUBLICATIONS

Troyer, D.L. et al. "A Novel Method for Preparing Histology Slides without a Microtome", Anat. Histol. Embryol. vol. 31, 2002, pp. 129-131.

(Continued)

*Primary Examiner* — Lyle Alexander
*Assistant Examiner* — Bryan Kilpatrick
(74) *Attorney, Agent, or Firm* — Sherry Austin (57) ABSTRACT

The application relates to a sample holder (110) and a system (100). The application also relates to a method for processing a biological sample (S) and use of the sample holder or of the system in an analytical method or a diagnostic method. The sample holder (110) comprises a tubular member (111) with a wall that is at least locally transparent and at least locally permeable for reagents, wherein the tubular member consists at least partially of a transparent material.

12 Claims, 4 Drawing Sheets

(51) Int. Cl.
*G01N 1/31* (2006.01)
*A61B 10/02* (2006.01)

(52) U.S. Cl.
CPC ....... *A61B 10/0233* (2013.01); *B01L 2200/10* (2013.01); *B01L 2200/16* (2013.01); *B01L 2300/0654* (2013.01); *B01L 2300/0681* (2013.01); *B01L 2300/0838* (2013.01); *B01L 2300/0858* (2013.01); *B01L 2300/12* (2013.01); *B01L 2400/0406* (2013.01); *B01L 2400/0472* (2013.01)

(56) References Cited

U.S. PATENT DOCUMENTS

| | | |
|---|---|---|
| 4,966,707 A | 10/1990 | Cussler |
| 5,919,356 A | 7/1999 | Hood |
| 5,968,436 A | 10/1999 | Takezaki |
| 6,411,434 B1 | 6/2002 | Eastman |
| 6,440,086 B1 | 8/2002 | Hohenberg |
| 2002/0108957 A1 | 8/2002 | Studer |
| 2003/0049833 A1* | 3/2003 | Chen ................. B01L 3/502 |
| | | 435/287.2 |
| 2007/0163942 A1 | 7/2007 | Tanaka |
| 2008/0070295 A1 | 3/2008 | Peltier |
| 2010/0167338 A1 | 7/2010 | Amano |
| 2010/0284014 A1 | 11/2010 | Baba |
| 2012/0016260 A1* | 1/2012 | To .................. A61B 10/06 |
| | | 600/562 |
| 2013/0182318 A1 | 7/2013 | Eastman |

FOREIGN PATENT DOCUMENTS

| | | |
|---|---|---|
| JP | 2006047191 A | 2/2006 |
| JP | 2002214093 A | 7/2007 |
| WO | 200053228 A2 | 9/2000 |

OTHER PUBLICATIONS

Provo-Klimek, Judy A. et al "A Novel Method for Preparing Histology Slides to Integrate the Teaching of Gross and Microscopic Anatomy", JVME, vol. 29 No. 3, 2002, pp. 137-141.

Xiao, Jun et al "A new chamber method for mounting tissue sections", Journal of Neuroscience Methods, vol. 144, 2005, pp. 235-240.

* cited by examiner

SAMPLE HOLDER FOR BIOLOGICAL SAMPLES

CROSS-REFERENCE TO PRIOR APPLICATIONS

This application is the U.S. National Phase application under 35 U.S.C. § 371 of International Application No. PCT/EP2015/064677, filed on Jun. 29, 2015, which claims the benefit of European Patent Application No. 14175012.5, filed on Jun. 30, 2014. These applications are hereby incorporated by reference herein.

FIELD OF THE INVENTION

The invention relates to a sample holder for holding a biological sample, for example during an optical examination thereof. Moreover, it relates to a system and a method for processing a biological sample.

BACKGROUND OF THE INVENTION

Biological samples such as a tissue biopsy are typically prepared by embedding the sample in paraffin, cutting slices thereof, and disposing these on a microscope slide. As this procedure is time consuming and laborious, an alternative approach has been proposed in literature in which the sample is transferred from a biopsy to a microscope slide with the help of an adhesive on the slide (D. L. Troyer et al., "A Novel Method for Preparing Histology Slides Without a Microtome", Anat. Histol. Embryol. 31, 129-131, 2002).

JP 2006 047191 A discloses a sample container being made up of a straw-like capillary which has an uniform outside diameter, and whose one or both aperture edges are closed by using a pressure bonding process, for improving its handlability and appropriately and reproducibly carrying out the cooling process for cryopreservations.

GB 2 289 222 A discloses a device for collecting flatus gas from a human or animal subject, the device comprising a gas-tight collecting tube for insertion into the rectum of the subject and retaining means comprising a pair of O rings locatable in the subject's inter-sphincter groove, for retaining the device in the subject with the O rings, providing a gas-tight seal. The end of the tube inserted into the subject is apertured and covered with a gauze filter to prevent the ingress of solid matter. This end of the collection tube is also covered with a gas permeable bladder with the distal end of the tube being connected to a gas-tight collecting bag.

U.S. Pat. No. 5,919,356 A discloses a portable device for sampling fluid. The device has a puncture device attached to a housing which has an interior and exterior wall. The housing is in fluid communication with the syringe and contains a filtration device comprised of at least one U-shaped hollow fiber membrane. The device also includes a collection chamber. Also in the device is a sensing device including a further hollow fiber membrane, the first and second ends each connected to a first and second plug. Each of the plugs contacts the interior wall of the housing. The further hollow fiber membrane contains a sensing agent. The device is arranged so that a sample is collected through the puncture device and is passed through the filtration device where is it passed through the one or more U-shaped hollow fiber membrane to the collection chamber. From the collection chamber it is passed through the hollow fiber membrane which contains the sensing agent device before being passed to a syringe.

US 2007/0163942 A1 discloses a hollow fiber membrane module comprising a large number of hollow fiber membranes contained in a cylindrical case, wherein one end of each hollow fiber membrane, which is left open, is fixed to the cylindrical case, while the other ends of the hollow fiber membranes are divided into more than one small bundles, with the ends, contained in separate small bundles, being kept together and plugged.

US 2008/0070295 A1 discloses a flask for preparing a fixer-based cytological suspension. The flask is equipped with a filtering element at least partly immersed in the suspension. The filtering element is in the form of a basket-forming filtering material web, whereof the periphery is fixed on the flask and whereof the center is connected to a tube, extending towards the opening of the flask, associated with a position-maintaining element in the flask and adapted to allow through a pipette for drawing the suspension.

SUMMARY OF THE INVENTION

In view of the above, it was an object of the present invention to provide means that allow for an alternative and preferably simpler handling of biological samples such as a biopsy.

This object is addressed by the invention as defined in the independent claims. Preferred embodiments are defined in the dependent claims.

A first aspect of the application relates to a sample holder for holding a biological sample such as a tissue section and/or cell agglomerate that shall be subjected to some processing. The processing may for example comprise a fixation, staining and/or examination of the sample. The sample holder comprises a tubular member with a wall that is at least locally transparent and that is further at least locally permeable for reagents. The tubular member consists at least partially of a transparent material.

The sample holder has the advantage that it allows for a simple and fast processing of a biological sample. This is because such a sample simply has to be taken up by the tubular member of the sample holder in order to bring it into a condition allowing for visual inspection while at the same time being accessible for an exposure to reagents. Moreover, the sample holder allows for an efficient processing of a biological sample, since no sectioning or microtoming is required and there is no loss of sample material during sample processing. In addition, the sample holder allows for an environmental friendly processing of a biological sample, since paraffination is not necessary and environmental hazard is reduced.

The sample holder may consist essentially or even completely of the tubular member, which provides for a simple and cost-effective design. The sample holder may also comprise additional components such as pieces of a housing or means for handling the tubular member. This allows for the integration of the sample holder into other devices and/or for a more convenient handling of the sample holder.

The tubular member may in general have any shape as long as some cavity is provided that can accommodate a biological sample. Typically, the tubular member will have a substantially straight elongated cavity, particularly a cylindrical cavity, wherein the tubular member and/or the cavity may have a circular, elliptical, polygonal or arbitrary cross section. A straight chamber can readily be produced, e.g. by extrusion, and it allows for an easy filling with sample material. The outer shape of the tubular member may correspond to the shape of said cavity (increased in dimension by the thickness of the walls), i.e. it may for example be cylindrical, too. The cavity of the tubular member will typically be open to the outside at at least one end to allow for the uptake of the sample. Preferably the cavity will be open at another end, too, to allow for the venting of air during the filling of the tubular member with a biological sample.

The transparency of (a part of) the wall of the tubular member shall be such that it allows for the visual inspection of the interior, i.e. of a sample accommodated in the sample holder. To minimize optical distortions, the wall should preferably have a regular and/or simple geometry in the region of its transparency, for example a planar or cylindrical shape.

Permeability of (a part of) the wall of the tubular member shall be such that reagents to which a sample shall be exposed can pass from the outside through the wall and reach the sample in the interior cavity of the tubular member. The permeability is preferably such that fluid reagents can pass through the wall (in one or both directions), for example gaseous reagents or reagents that are solved in a solution, e.g. staining antibodies, because many practically relevant reagents are fluids. The wall may comprise a plurality of apertures or pores, particularly apertures or pores with a diameter of less than about 10 nm, less than about 100 nm, less than about 1 µm, less than about 10 µm, or less than about 100 µm. The mentioned diameters have the advantage that a selection of components which may pass the wall is achieved. Additionally or alternatively, the spatial density of the apertures or pores may preferably be at least about 1 aperture/mm$^2$, at least about 100 apertures/mm$^2$, at least about 10000 apertures/mm$^2$, or most preferably at least about 1000000 apertures/mm$^2$. The mentioned densities have the advantage that high flow rates through the wall may be achieved while at the same time a sufficient stability of the wall is maintained.

The regions where the wall of the tubular member is transparent and where it is permeable may be distinct or may (at least partially) overlap. Preferably, the same region of the wall is at the same time transparent and permeable. Most preferably, the complete tubular member is constituted by a wall that is both transparent and permeable for reagents. This has the advantage that the whole tubular member has a simple design and can be built with a single material.

The sample holder may optionally be a disposable element which is e.g. used only once for the processing of a single sample. Thus a contamination between samples and/or reagents of different applications can be prevented.

A second aspect of the application relates to a system for processing a biological sample, said system comprising the tubular member of the first aspect of the application and at least one "supplementary component", each of the at least one supplementary component having a bearing that can couple to at least a part of the tubular member of the sample holder.

The system and the sample holder may optionally be considered as different elements, particularly if they can independently be manufactured, stored, and/or sold, that may independently be claimed.

An advantage of the system is that its "supplementary component" may provide additional functionality, for example the transfer of sample and/or reagents from an external source into the sample holder. Further advantages of the system are the same as discussed above with respect to the sample holder according to the first aspect of the application.

"Coupling" of the bearing of the system to the tubular member of the sample holder may comprise a mutual mechanical attachment. Additionally or alternatively, it may comprise a functional coupling that allows for the exchange of material (sample, reagents etc.) between tubular member and supplementary component.

The supplementary component may preferably be a re-usable element or device, which is economically and ecologically advantageous.

A third aspect of the application relates to a method for processing a biological sample, said method comprising the following steps:
  Transferring the sample into a sample holder having a tubular member with a wall that is at least locally transparent and at least locally permeable for reagents, preferably a sample holder of the first aspect of the application.
  Exposing the sample holder to at least one reagent such that this reagent can reach the sample within the sample holder through the permeable wall of the tubular member.

The method has the advantage that it allows for a simple and fast processing of a biological sample. The method also allows an efficient, environmental friendly processing of a biological sample. These advantages have already been discussed above in the first aspect of the application.

A fourth aspect of the application relates to use of the sample holder and/or the system according to the first and/or second aspects in an analytical method or a diagnostic method.

Using the sample holder and/or the system according to the first and/or second aspects allows for a simple and fast analytical method or diagnostic method. The use also allows for an efficient, environmental friendly analytical method or diagnostic method. Similar advantages are discussed above in the first aspect of the application.

The sample holder, the system, the method, and the use are based on the concept that a sample is accommodated in a tubular member being at least locally transparent and at least locally permeable such that reagents can reach a sample through said wall. Explanations and advantages provided for one of these aspects are therefore analogously valid for the other aspects, too.

In a first preferred embodiment, the tubular member of the sample holder may have an interior diameter ranging between about 0.2 mm and about 2 mm, preferably between about 0.5 mm and about 1.5 mm (wherein said diameter shall by definition be the diameter of the cross section of the hollow cavity of the tubular member, said cross section being perpendicular to the axis of extension of said cavity; in case of a non-circular cross section, its "diameter" shall be defined as the largest distance between two points on the border of the cross section). The described preferred values of the diameter allow for an in-depth inspection of a sample within the tubular member by optical methods. The length of the tubular member (measured in a direction perpendicular to the diameter) typically ranges between about 2 mm and about 50 mm.

The tubular member may in general consist of any material or materials having the properties required in the application at hand, for example a sufficient stability, compatibility with biological material, transparency and/or permeability. Preferably, the tubular member consists at least partially of a membrane, particularly a porous polymer membrane. The membrane may have a plurality of pores and/or a thickness of less than about 0.2 mm, preferably less than about 100 µm, or preferably less than about 50 µm.

Preferred materials comprise micro-porous materials, filtration membranes, track-etched materials, membranes made by phase separation (e.g. thermal- or reaction-induced phase separation), or micro-molded membrane materials with a well-defined and regular pore size. Such materials can be polymers, ceramics, glass and/or silicon. Glass and silicon porous materials can be manufactured by etching, while polymer membranes are either made by replication or by phase separation. Membranes in general and the listed membranes in particular have the advantage that they can readily be produced with desired pore sizes and dimensions. Moreover, they are typically compatible to biological samples.

According to another embodiment, the sample holder may comprise at least one fluidic channel through which a sample in the tubular member is accessible. The fluidic channel may particularly have a diameter of about 1 µm to about 1 mm. It may for example be an aperture in the wall of the tubular member. Most preferably, the tubular member has a plurality of fluidic channels (apertures) allowing reagents to access a sample substantially through an area.

In the aforementioned embodiment, a variety of materials can be used in which (micro) fluidic channels are artificially created in the wall of a tubular member. Suitable materials for this purpose are glass, silicon, silicone rubber thermoplastic polymers, like polypropylene, polystyrene, polymethylmethacrylate, polycarbonate, polyester, polyamide, polyurethane, cyclo-olefin (co-)polymers, thermoplastic elastomers based on polyether-ester, amides, or olefins, in addition to cross-linked polymers, like silicones, acrylates, urethanes, epoxies, polyimides, cyclenes, methacrylates, acrylamides, etc. Possible procedures for manufacturing the aforementioned materials with (micro) fluidic channels comprise casting, extrusion, thermoforming, injection molding, micromolding reaction injection molding, laser machining, lamination. Materials with fluidic channels in general and the listed embodiments in particular have the advantage that they can readily be integrated and/or produced in one piece with other devices and components, for example with housings.

In the system for processing a biological sample according to the second aspect of the application, at least one of the at least one "supplementary component" may be or comprise a transfer device for transferring a sample from an extraction device into the sample holder, wherein said transfer device comprises a transfer channel with a first end (its "bearing") to which the sample holder can be connected and with a second end to which the extraction device can be connected. The system may or may not include the extraction device for extracting a biological sample from a subject. The extraction device may be a device commonly used in the art for extracting a biological sample from a subject. Multiple types of such extraction devices can be used including needles such as a biopsy needle. Most preferably, there can be a closed connection between the sample holder and the first end and/or between the extraction device and the second end in order to prevent the escape of material. When an extraction device is connected to the second end and a sample holder is connected to the first end, sample material can be transferred from the extraction device into the sample holder via the transfer channel of the device. After such a transfer, the sample holder may be disconnected from the transfer device and used as desired in the application at hand. Usage of a transfer device has the advantage that the means for transferring sample from an extraction device into the sample holder can be reused many times while the sample holder can have a simple and cost-effective design.

The first end and/or the second end of the aforementioned transfer channel may particularly comprise openings corresponding to the shape of the sample holder (or, more specifically, its tubular member) or of the extraction device, respectively. Moreover, these ends may preferably be made of some elastic material, e.g. rubber, that can compensate for tolerances and provide for a sealed connection.

According to another embodiment, at least one of the at least one "supplementary component" of the system may be or comprise an extraction device (e.g. a biopsy needle) for extracting a sample from a subject, wherein said extraction device features a bearing for accommodating the sample holder such that an extracted sample is taken up into the sample holder. Hence no additional transfer of a sample (e.g. a biopsy) from the extraction device into the holder is necessary. Preferably, the sample holder (with the sample) can after the extraction procedure be removed from the extraction device for further processing (e.g. staining, optical investigation etc.).

According to another embodiment, the system may (additionally or alternatively) comprise an optical apparatus for generating images of a sample in the sample holder. The optical apparatus may for example comprise a microscope for visual inspection by a user, particularly a digital scanning microscope with means for generating images of a sample. Images may for example be generated by confocal microscopy of a sample in a stationary or a moved sample holder. Usage of the sample holder in connection with such an optical system is possible because of the transparency of the tubular member.

In still another embodiment, at least one of the at least one "supplementary component" of the system may be or comprise a container with a bearing for exchangeably or permanently accommodating the sample holder. The size and design features of the sample holder can then be reduced to a minimum that is necessary for the function of accommodating a sample, while additional functionality can be provided by the container. This functionality may for example comprise a better handling of the sample holder by providing a component that can be gripped by a user. Additionally or alternatively, the functionality may comprise an optical adaptation of the sample holder to inspection means such as a microscope. The container may be designed to accommodate just one sample holder or for accommodating two or more sample holders at the same time. Moreover, the sample holder can exchangeably be accommodated, i.e. such that it can deliberately be introduced and/or removed from the container by a user. Alternatively, the sample holder may permanently be accommodated in the container, for example if it is an integral part thereof.

In an optional further development of the above embodiment, the sample holder is accommodated in the container such that it can rotate relative to the container about its axis of extension. Additionally or alternatively, the sample holder may be movable in axial direction within the container (i.e. in the direction of its axis of extension). In these cases the container can remain stationary (e.g. attached to a microscope table) while all portions of a sample in the sample holder can be inspected by rotating and/or shifting the sample holder relative to the container.

In another preferred embodiment of the system with a container, the bearing of said container comprises a cavity for taking up the sample holder wherein the latter is embedded in a fluid filling the (rest of the) cavity. The fluid-filled space of the cavity may for example comprise reagents to which the sample in the sample holder shall be exposed, thus allowing for a well controlled exchange of reagents with the sample holder. In this case there will preferably be means for introducing (fresh) reagent into the cavity and/or means for removing (used) reagents from the cavity. In a preferred embodiment the reagent fluid is actuated by a pumping means to enhance penetration of the sample. The fluid circuitry can be designed as micro fluidic device to achieve high convection while using only small amounts of reagent. In another example, the cavity may be filled with an index-matching fluid that is used to adapt the indices of optical refraction of the wall (or the transparent part of the wall) of the tubular member and/or of the container such that optical inspection of the sample is facilitated.

The container may in general have any shape suited to accommodate the sample holder. It may for example comprise two flat plates (of which at least one should be at least partially transparent) that are disposed a distance apart and sandwich the sample holder in between (preferably in a space filled with an index-matching fluid). This provides for a simple design of the container that can usually be realized with standard components. In another embodiment, the container may comprise a substrate with a bearing having a bore with the shape and size of the tubular member of the sample holder (including some appropriate oversize to allow for a play and to compensate for tolerances in the dimensions of sample holders). The remaining gap between the outside of the tubular member and the wall of said bore may optionally be filled with a fluid, particularly an index-matching fluid. This provides for a container design with few components (particularly a single piece) that can readily be handled.

In another embodiment, the container may comprise a fluidic system for controlling fluid flow around the tubular member of the sample holder. Thus a controlled sequential provision of different reagents can for example be achieved, or the application of a forced convection to enhance reagent transport.

In the third aspect of the application, which relates to a method for processing a biological sample, the method may optionally further comprise the step of optical examination of the sample in the sample holder. This examination may for example be done with the help of a microscope, wherein the sample holder may be placed directly under the microscope or indirectly within a container of the kind described above.

The reagents to which the sample holder may be exposed may comprise a fixation/permeabilization reagent, a washing solution and/or a staining reagent, and/or an anti-quenching solution. Fixation, permeabilization and staining are important steps of preparing a biological sample for further analysis, particularly optical analysis under a microscope. The sample in the sample holder may for example be exposed to a fixation reagent in order to "freeze" the biological processes in the sample and avoid degradation of biomolecules. Thereafter, the sample may be additionally permeabilized and exposed to one or more staining reagents allowing for the detection of tissue components of interest, for example of tumor cells. In general, staining may be done with reagents and protocols as used in histopathology, cytopathology, immuno-histochemistry and in-situ hybridization, in particular for oncology diagnostics, as for instance identification of cancer cells or biomarkers in cells.

The method may further optionally comprise the step of extraction of a region of interest from the sample in the sample holder. This respective region of interest may for example be identified with the help of a microscope under which the sample holder is examined. The extracted part of the sample may then be investigated by molecular diagnostic techniques, like sequencing, for identifying molecular changes in the cells for example cancer cells of the sample.

The extraction of a region of interest from the sample can comprise the following steps: identifying a position and axial extension of the region of interest of the sample, marking the edges of that region, physical removal of that region by cutting the sample at the predetermined positions. The separated region of interest can then be placed in a container and exposed to a procedure for nucleic acid extraction, purification, amplification and detection. The cutting can be done with the tubular member holding the sample. This can be facilitated with a holding device of the tubular member for support. The cutting can be done with a scalpel or similar device.

In the fourth aspect of the application, which relates to use of the sample holder and/or the system as described above in an analytical method or a diagnostic method, the analytical method or diagnostic method may be for example biological sample analysis, molecular diagnostics, chemical sample analysis, food analysis, and/or forensic analysis. During biological sample analysis, preferably molecular diagnostics, diseases or preferably cancer may be diagnosed.

In an embodiment where the biological sample is biopsy, there is no loss of biopsy during the diagnostic method. Therefore, the amount of biopsy taken from a subject is reduced and thus the pain of taking the biopsy is reduced.

BRIEF DESCRIPTION OF THE DRAWINGS

These and other aspects of the invention will be apparent from and elucidated with reference to the embodiments described hereinafter. In the drawings.

Like reference numbers or numbers differing by integer multiples of 100 refer in the Figures to identical or similar components.

DETAILED DESCRIPTION OF EMBODIMENTS

Pathology diagnostic investigation of patient material (e.g. tissue and cells) is the basis of many treatment decisions, in particular in oncology. Typically thin slices from a biopsy are presented on microscope slides and stained according to certain protocols to visualize the morphology of the tissue, e.g. by Hematoxylin-Eosin staining (H&E). More recently in situ staining for disease-specific biomarkers is being developed for companion diagnostics of targeted drugs, based on the specific binding of antibodies to antigens, for example proteins, present in the tissue, so-called immuno-histochemistry (IHC), and hybridization of designed sequences of nucleotides to parts of a chromosomes or genes (in-situ hybridization, ISH).

With increasing understanding of the role of genetic mutations in cancer cells molecular diagnostics ("MDx") are becoming an essential part of pathology for selecting targeted therapies and predicting treatment response. This may be done by q-PCR micro-array and/or sequencing (Sanger or next generation) on the tissue. For the sensitivity and specificity of the MDx analyses it is of essential importance to select only relevant areas of the tissue slice. Dilution by non-cancerous tissue/cells leads to misdiagnosis. Lack of sufficient tumor material is a related problem leading to false negatives or invalid results.

Cutting biopsies with a microtome for visual inspection after staining creates a lot of effort in the pathology lab and leads to loss of valuable (and in general low amounts of) tissue. After inspection sections need to be selected for further analysis by molecular diagnostic techniques. Sample selection requires sufficient amount and purity of the sample with respect to tumor cell content. Starting from slices means selection from multiple sections for sufficient input. With decreasing size of biopsies and increasing number of biopsies per patient and increasing number of MDx tests per sample the problem is becoming bigger. Especially small biopsies from core needles or cells from fine needle aspirates can create a problem that during the required sectioning by microtome a relatively large amount of sample is lost or wasted. This limits the possibility of doing multiple MDx tests and/or the quality of the MDx tests and increases the effort of collection of input material. An alternative would be the use of larger biopsy cores which however is very impactful for the patient, e.g. painful. The necessity of microtoming tissue creates the need for freezing or alternatively paraffin embedding. Both procedures have their downsides, either of practical nature, like freezing which requires special skills and does not conserve the tissue for longer term storage, or paraffin embedding which creates a significant effort and environmental impact of using harmful solvents, as well as leading to long throughput times that do not allow direct feedback for instance for surgical procedures. Also when algorithms are used to (quantitatively) interpret a staining, e.g. in the case of use of a Digital Pathology system, fixation/permeabilization and staining procedures should be standardized, otherwise the algorithm-based assay result becomes unreliable.

To address the above issues, an approach is suggested here that may in a particular embodiment comprise the following steps: A biopsy of interest is transferred from a needle or some other extraction device into a thin-walled, cylindrical tubular member of a "sample holder" that is permeable for fluids. The sample holder with the biopsy inside may then be immersed in a reagent such as a fixation liquid, or alternatively the fluid is flown through by coupled microfluidic channels. Fixation is achieved due to the diffusion of fixative through the walls of the tubular member and inside the sample. After fixation the sample holder may be transferred to a desired staining station. Staining protocols and probes depend on application. In general this procedure may be followed for advanced cancer diagnostics, including advanced staining and/or molecular diagnostic testing, and on top of the routine biopsy procedure for diagnosis of cancer. Staining protocols typically comprise incubation with a probe followed by a washing step.

FIGS. 1-6, 8 and 9 schematically show a system 100 comprising an embodiment of a sample holder 110 of the kind described above.

Figure 1:
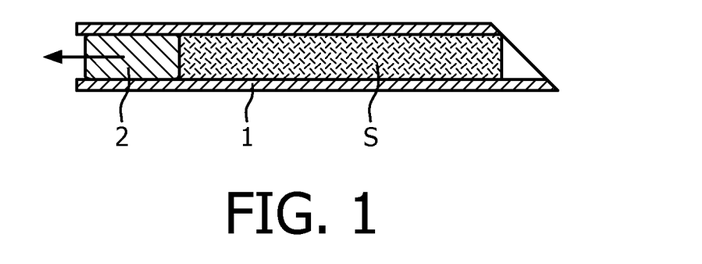
FIG. 1 schematically shows a section through a needle with a biopsy sample.

In particular, FIG. 1 shows a section along the axis of extension of a core needle 1 comprising a biological sample S such as a biopsy taken from some tissue of interest. The sample S can be moved within a cavity of the needle 1 by movement of a piston 2.

Figure 2:
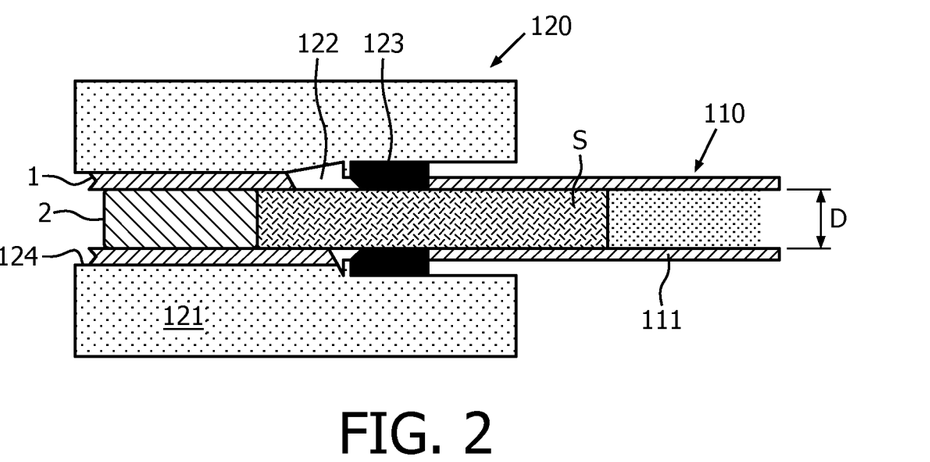
FIG. 2 schematically shows a cross section through a transfer device to which the needle of FIG. 1 and a sample holder according to an embodiment of the invention are coupled.

FIG. 2 illustrates the transfer of the sample S from the core needle 1 into a sample holder 110 according to an embodiment of the invention. The transfer takes place with the help of a "transfer device" 120 comprising a body 121 featuring a transfer channel 122 with a first end 123 and a second end 124. The first end 123 is designed as a bearing to allow for a closed connection to the sample holder 110 (or, more particularly, to the tubular member 111 of such a sample holder). The second end 124 is designed to allow for a fluid-tight connection to an external extraction means such as the core needle 1.

When both the core needle 1 and the sample holder 110 are connected to their respective ends, the sample S can be transferred from the core needle 1 via the transfer channel 122 into the interior cavity of the tubular member 111 of the sample holder 110 by pushing the piston 2. After completion of this transfer, the sample holder 110 can be disconnected from the transfer device.

The walls of the tubular member 111 are permeable for liquids. They can be made of membrane material that is optically transparent. One example is track-etched polycarbonate (e.g. Isopore of EMD Millipore, US). The optical transparency is only required in the wet state during optical inspection. For improved transparency index matching liquids can be introduced. The permeability of the membrane should be high for the reagents used during processing. The penetration of the reagents into and inside the sample specimen is mainly determined by diffusion. The permeability of the membrane material should be of a similar order as the diffusion rate inside the sample to not increase the processing times significantly. Micro-porous materials are preferred. Filtration membranes are available in different thicknesses and pore diameters and densities. Alternative to the track-etched materials are membranes made by phase separation, e.g. thermal- or reaction-induced phase separation, or micro-molded membrane materials with a well-defined and regular pore size.

The biopsy S in the sample holder 110 can be directly immersed in fixation buffer (buffered formalin in water) to preserve the morphology and freeze bio-molecular processes. Fixation is rapid due to the small dimensions. After fixation the biopsy in the sample holder can be directly forwarded to pathological staining. Paraffin embedding is not necessary since the investigation will be carried out on the whole biopsy inside the sample holder and no microtoming is done. The staining procedures need to be adjusted for the pertinent incubation and washing steps as a consequence of the geometry that is different from standard slices of 4-8 micrometer. The increased thickness will lead to longer timescales for the processes. However, depending on the type of microscopical investigation the penetration depth of staining can be limited to a few micrometers as well. In a preferred embodiment the sample is investigated as a cylindrical specimen with line illumination and rotation of the sample. This is indicated in FIG. 3 as an example.

Figure 3:
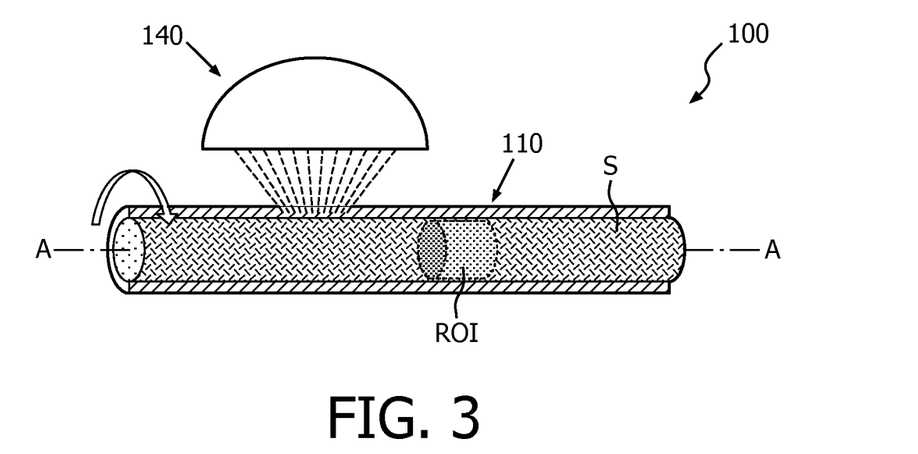
FIG. 3 schematically shows an embodiment of a system for the optical examination of the sample by rotation and stepwise axial movement of the sample holder.

FIG. 3 schematically shows a system 100 comprising the sample holder 110 and a microscope 140 for the optical investigation of the sample S inside the sample holder 110. In this embodiment, the sample holder 110 can be rotated about its axis A of extension while being optically monitored at a point or along a line. Moreover, the sample holder 110 can be moved in steps in the axial direction A to allow for the consecutive inspection of different axial sections of the sample.

By varying the depth of focus a 3D image of the sample S can be created. Analysis of the image can provide an area or volume of interest, ROI, for molecular diagnostics. This will typically be a section in the axial direction which can easily be removed from the tubular member 111 by cutting. In this way no sample is lost for MDx analysis, no matter how tiny the biopsy is. Subsections can be made for multiple analyses. Preserving the overall integrity of the biopsy allows a precise mapping of the images on the position of the tumor from which the biopsy has been taken. Additionally or alternatively, the sample holder may optionally comprise a window (not shown) at an intermediate position between its left and right ends. The region of interest ROI may then be positioned at this window by moving the whole sample appropriately in axial direction, and it may be removed through said window without affecting the remainder of the sample.

As explained above, image acquisition can be done directly on the tubular member 111 after staining. The curved shape of this member can however affect the focus quality in direct observation. To reduce this effect the tubular member 111 can be inserted between two flat substrates with an index-matching liquid in between, or alternatively in a substrate with a bearing comprising an opening (bore) that matches the diameter of the tube. In this way conventional microscopes or digital scanners can be employed for image acquisition, and the microscopic investigation can be carried out in a more conventional confocal arrangement in which an x,y-scan is performed.

Figure 4:
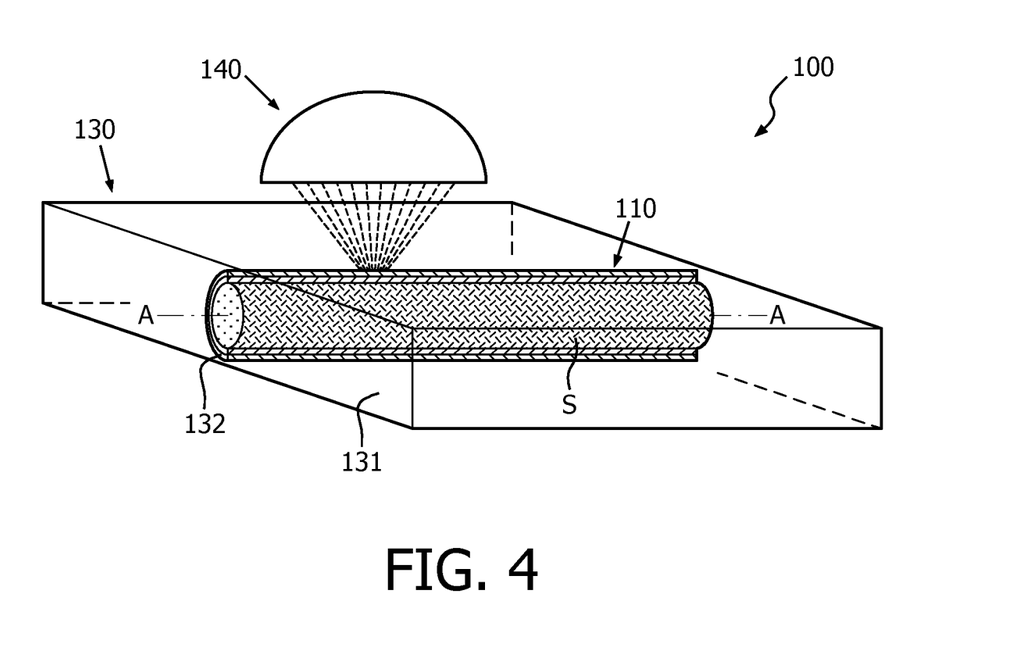
FIG. 4 schematically shows an embodiment of a system with a container for the accommodation of the sample holder during microscopic investigation.

FIG. 4 shows such an extension of the system 100 comprising a container 130 formed by a planar substrate 131 with a bearing 132 comprising a cylindrical bore in which the sample holder 110 can be inserted for investigation with the microscope 140. The substrate 131 is preferably made of a transparent material, particularly a material having a similar index of refraction as the tubular member 111 of the sample holder 110. Most preferably, the gap between the sample holder 110 and the bore of the bearing 132 may be filled with an index-matching fluid to allow for improved optical quality.

Figure 5:
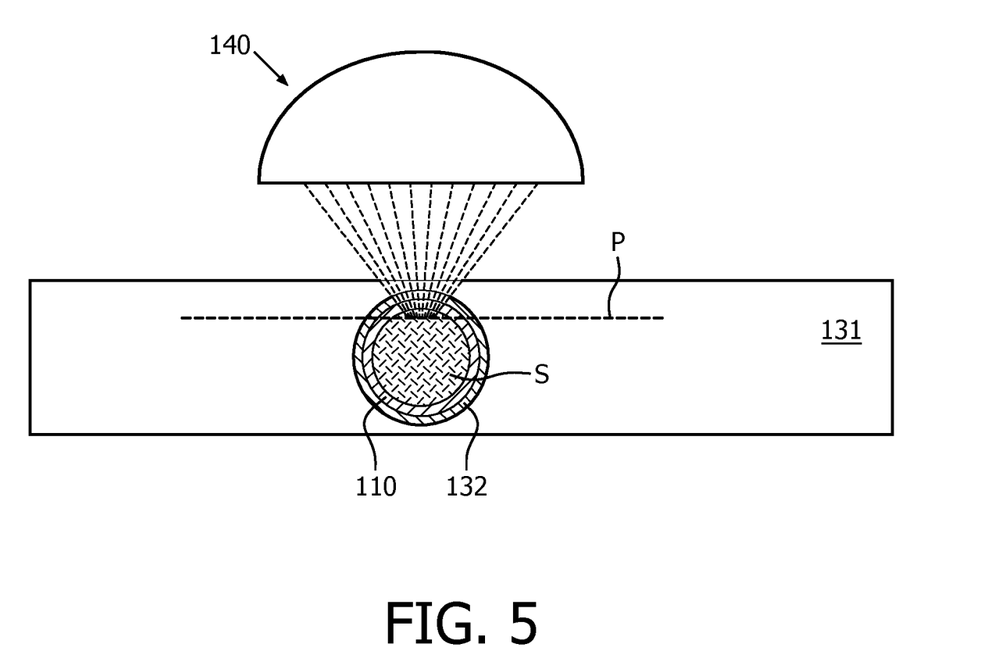
FIG. 5 schematically shows a section through the container with the sample holder during confocal scanning in a microscope.

FIG. 5 schematically shows a section through the container 130 with the sample holder 110 in a direction perpendicular to the axis A of extension of the sample holder. It illustrates the confocal scanning indicating possible focal planes P in the cylindrical biopsy S. Multiple focal planes can be scanned to obtain a quasi-3D image of the biopsy. From the image an area of interest can be obtained, indicating for instance a high concentration of tumor cells. This area of interest can be easily translated into a volume of interest, or zone of interest that can be removed from the cylindrical biopsy inside the container readily. The advantage of this approach is that no material is lost from the volume of interest in contrast to the conventional selection from individual slices on microscopy slides.

The tubular member 111 of the sample holder 110 typically has in interior diameter D of about 0.2 mm to about 2 mm. This may imply longer diffusion times as compared to tissue slices on a slide. However, it is not required to stain a sample S in the tubular member 111 to the full depth but rather to the depth of focus that is used in the image acquisition.

The arrangement with a container as depicted in FIGS. 4 and 5 can also be used for the fixation and staining of the specimen, where the index matching liquid is replaced by a fixation or staining solution.

Figure 6:
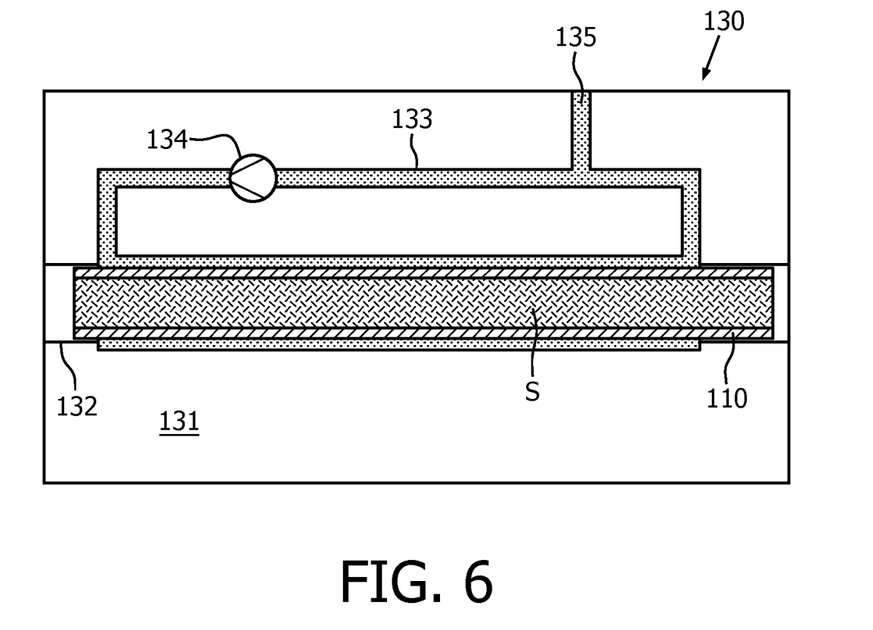
FIG. 6 schematically shows a container comprising a fluidic system for generating a convection of reagent fluid.

FIG. 6 shows in this respect a section through a medial plane of a preferred embodiment of the container 130. As above, the container comprises a bearing 132 with a bore in which a sample holder 110 with a specimen S is placed. Moreover, it comprises a fluidic system 133 that accommodates the sample holder 110 (or at least a part thereof). The fluidic system 133 comprises a fluid inlet/outlet 135 and a pumping device 134 for generating a convection of reagent fluid around the sample holder 110. The transition between the bearing 132 and the fluidic system 133 is preferably sealed (not shown).

Figure 7:
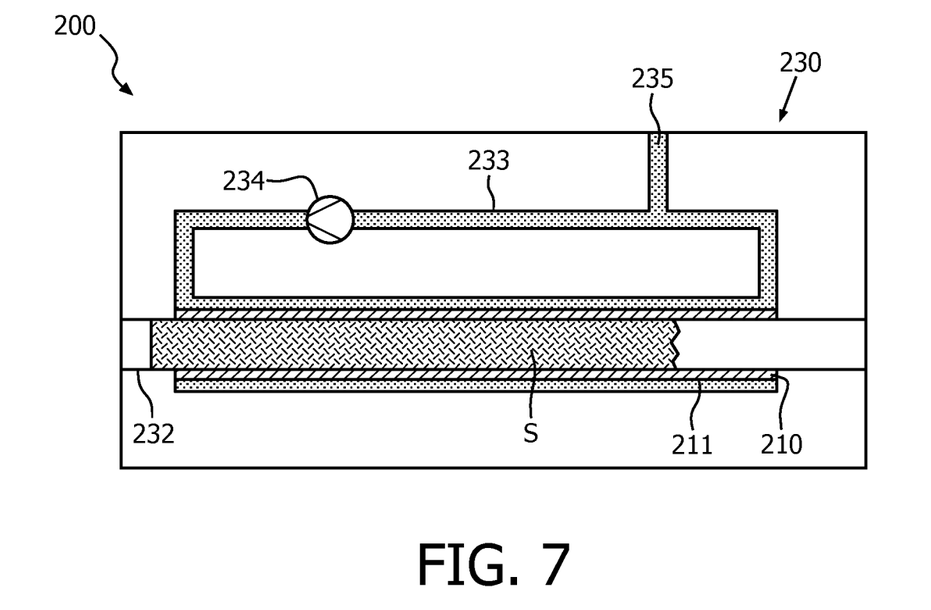
FIG. 7 schematically shows a container comprising a fluidic system and a permanently integrated sample holder.

FIG. 7 illustrates an alternative embodiment of a system 200 with a sample holder 210 and a container 230. The container 230 comprises a fluidic system 233 with an inlet/outlet 235, a pumping device 234, and a cavity 232 into which the tubular member 211 of the sample holder 210 is permanently integrated. The tubular member 211 may for example comprise a cylindrical wall that is integral with the material of the container and that comprises a plurality of apertures or fluidic channels through which reagents can reach a sample S in the interior of the sample holder 210. The permanent wall 211 hence takes the role of the membrane in the above embodiments.

Figure 8:
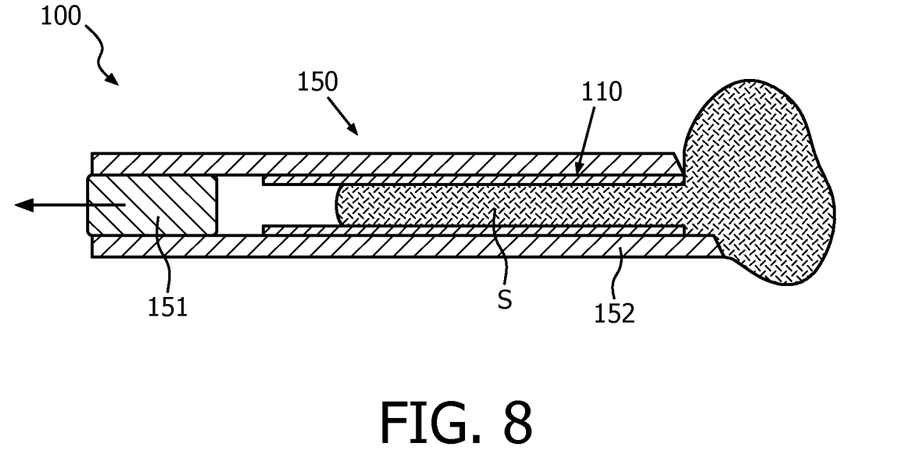
FIG. 8 schematically shows an embodiment of a system with an extraction device that can accommodate the sample holder of FIG. 2 during the uptake of a sample.
Figure 9:
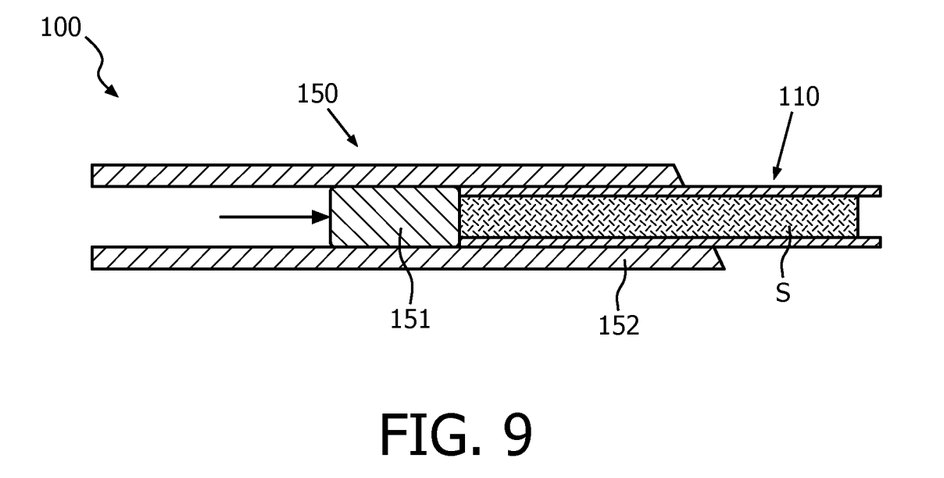
FIG. 9 shows the system of FIG. 8 during the subsequent ejection of the sample holder.

FIGS. 8 and 9 illustrate a further optional embodiment of the system 100. In this embodiment the system 100 additionally or alternatively comprises an extraction device, here a biopsy needle 150, with a bearing 152 for accommodating the sample holder 110 described in FIGS. 2-6. By retracting a piston 151 of the extraction device, a sample S can thus directly be drawn into the sample holder 110. This process is illustrated in FIG. 8.

FIG. 9 shows the subsequent ejection of the sample holder 110 together with the sample S from the extraction device 150. This ejection can for example be achieved with the help of the piston 151. The sample holder 110 can thereafter be used as desired, for example be transferred to a container 130 for optical examination.

The solutions can be actively pumped axially or radially across the specimen via the appropriate arrangement of fluidic channels. The channel dimensions can be kept small to reduce reagent consumption and achieve strong convective flow to enhance diffusion. The container 130 can be designed as microfluidic cartridge with the necessary interface for liquid supply (e.g. tubes and reservoirs) and actuation (e.g. pneumatic actuation or syringes).

In summary, embodiments of a method and a device have been described that allow pathological investigations on tissue without sectioning. The biopsy is transferred from e.g. a needle core into a dedicated tube to preserve the shape and avoid breakage. The tube is preferably made of an optically clear material that is permeable for chemical reagents to allow for fixation and staining of the tissue. The staining reactions are carried out with the fully intact biopsy. After staining the biopsy can be investigated by optical microscopy in brightfield or fluorescence or a digital scanning microscope. This can either be done by for example rotating the cylindrical sample with line illumination to investigate a large area, or alternatively the tube can be inserted into a substantially flat substrate with index-matching fluid for optical investigation with conventional means. The depth of focus can be varied to obtain information from layers beneath the surface of the biopsy and/or to obtain 3D information. By having the biopsy enclosed in a tube paraffination is not necessary and no sectioning is required which reduces the workload, environmental hazard and time to result and increases efficient usage of small samples. Selecting samples for further Molecular Diagnostics testing is more efficient as no material is lost by sectioning.

The approach can inter alia be applied in histopathology, biopsy taking, tissue processing, molecular pathology, in particular for patient stratification in oncology based on identification of molecular changes in cancer cells.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A system for processing a biological sample, the biological sample is biopsy, said system comprising:
   a sample holder including a tubular member for holding the biological sample therein, wherein the tubular member including a wall having at least one region composed of a material that is both transparent for optical examination of the biological sample within the tubular member and permeable for diffusion of at least one reagent through the wall to the biological sample within the tubular member; and
   at least one supplementary component, each of the at least one supplementary component having a bearing that can couple to at least a part of the tubular member of the sample holder.

2. The system according to claim 1, wherein the tubular member has an inner diameter (D) ranging between 0.2 mm and 2 mm.

3. The system according to claim 1, wherein the material of the wall includes at least partially:
   a membrane, particularly a porous polymeric membrane, through which the biological sample in the tubular member is accessible by the at least one reagent; and/or
   fluidic channels through which the biological sample in the tubular member is accessible by the at least one reagent.

4. The system according to claim 1, wherein the at least one supplementary component includes at least one of:
   an extraction device for extracting the biological sample from the subject, the extraction device having a bearing for accommodating the sample holder such that the biological sample as extracted from the subject is taken up by the sample holder;
   a transfer device for transferring a sample from a core needle into the sample holder, the transfer device including a transfer channel with a first end to which the sample holder can be connected and with a second end to which the core needle can be connected; and
   a container with a bearing for exchangeably or permanently accommodating the sample holder.

5. The system according to claim 1, further comprising an optical apparatus for generating images of the biological sample in the sample holder.

6. The system according to claim 1, wherein the at least one supplementary component includes a container with a bearing for exchangeably or permanently accommodating the sample holder and that the sample holder can be or is rotatably accommodated in the container and/or that the sample holder is movable in axial direction within the container.

7. The system according to claim 1, wherein the at least one of the supplementary component includes a container with a bearing for exchangeably or permanently accommodating the sample holder and that the bearing of the container defines a cavity for being filled at least partly with a fluid and for taking up the sample holder for being immersed in the fluid.

8. The system according to claim 1, wherein the at least one supplementary component includes a container with a bearing for exchangeably or permanently accommodating the sample holder and that the container includes a substrate with a bearing that defines a bore having the shape of the tubular member of the sample holder.

9. The system according to claim 1, wherein the at least one supplementary component includes a container with a bearing for exchangeably or permanently accommodating the sample holder and that the container includes a fluidic system for controlling fluid flow around the tubular member of the sample holder.

10. A method for processing a biological sample, the biological sample is biopsy, said method comprising the following steps:
    transferring the biological sample into a tubular member of a sample holder, the tubular member including a wall having at least one region composed of a material that is both transparent for optical examination of the biological sample within the tubular member and permeable for diffusion of at least one reagent through the wall to the biological sample within the tubular member; and
    exposing the tubular member to the at least one reagent such that the reagent may diffuse through the wall to the biological sample in the tubular member.

11. The method according to claim 10, further comprising at least one of the following steps:
    optical examination of the biological sample in the tubular member; and
    extracting a region of interest of the biological sample from the tubular member.

12. The method according to claim 10, wherein the at least one reagent include at least one of a fixation reagent, a permeabilization reagent, washing reagent, an anti-quenching reagent and a staining reagent.

* * * * *